(12) United States Patent
Barrett et al.

(10) Patent No.: US 8,309,307 B2
(45) Date of Patent: Nov. 13, 2012

(54) HIGH RESOLUTION CHROMOSOMAL MAPPING

(75) Inventors: Michael Thomas Barrett, Mountain View, CA (US); Michael P. Caren, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/286,975

(22) Filed: Nov. 1, 2011

(65) Prior Publication Data

US 2012/0053082 A1    Mar. 1, 2012

Related U.S. Application Data

(62) Division of application No. 11/400,481, filed on Apr. 7, 2006, now Pat. No. 8,058,055.

(51) Int. Cl.
*C12Q 1/68*    (2006.01)
*C12M 1/34*    (2006.01)
*C12M 3/00*    (2006.01)
*C07H 21/02*   (2006.01)
*C07H 21/04*   (2006.01)

(52) U.S. Cl. .................. 435/6.1; 435/91.2; 435/287.2; 536/23.1; 536/24.33

(58) Field of Classification Search .................. 435/6.1, 435/287.2; 536/23.1, 24.33
See application file for complete search history.

(56) References Cited

U.S. PATENT DOCUMENTS

| | | | |
|---|---|---|---|
| 5,225,326 A | 7/1993 | Bresser et al. | |
| 5,665,549 A | 9/1997 | Pinkel et al. | |
| 5,830,645 A | 11/1998 | Pinkel et al. | |
| 5,948,902 A | 9/1999 | Honkanen et al. | |
| 6,171,797 B1 | 1/2001 | Perbost | |
| 6,180,351 B1 | 1/2001 | Cattell | |
| 6,197,501 B1 | 3/2001 | Cremer et al. | |
| 6,221,583 B1 | 4/2001 | Kayyem et al. | |
| 6,232,072 B1 | 5/2001 | Fisher | |
| 6,242,266 B1 | 6/2001 | Schleifer et al. | |
| 6,251,588 B1 | 6/2001 | Shannon et al. | |
| 6,306,643 B1 | 10/2001 | Gentalen et al. | |
| 6,309,875 B1 | 10/2001 | Gordon | |
| 6,323,043 B1 | 11/2001 | Caren et al. | |
| 6,335,167 B1 | 1/2002 | Pinkel et al. | |
| 6,387,636 B1 | 5/2002 | Perbost et al. | |
| 6,406,849 B1 | 6/2002 | Dorsel et al. | |
| 6,410,243 B1 | 6/2002 | Wyrick et al. | |
| 6,420,180 B1 | 7/2002 | Bass | |
| 6,587,579 B1 | 7/2003 | Bass | |
| 6,589,739 B2 | 7/2003 | Fisher | |
| 6,599,693 B1 | 7/2003 | Webb | |
| 6,613,893 B1 | 9/2003 | Webb | |
| 6,656,740 B1 | 12/2003 | Caren et al. | |
| 6,691,042 B2 | 2/2004 | Weng et al. | |
| 6,756,202 B2 | 6/2004 | Dorsel et al. | |
| 2003/0054346 A1 | 3/2003 | Shannon et al. | |
| 2003/0162183 A1 | 8/2003 | Kincaid | |
| 2004/0002070 A1 | 1/2004 | Kincaid | |
| 2004/0009484 A1 | 1/2004 | Wolber et al. | |
| 2004/0086880 A1 | 5/2004 | Sampson et al. | |
| 2004/0101845 A1 | 5/2004 | Collins et al. | |
| 2004/0101846 A1 | 5/2004 | Collins et al. | |
| 2004/0191813 A1 | 9/2004 | Bruhn et al. | |
| 2004/0241658 A1 | 12/2004 | Barrett et al. | |
| 2004/0241663 A1 | 12/2004 | Peck et al. | |
| 2004/0259146 A1 | 12/2004 | Friend et al. | |

FOREIGN PATENT DOCUMENTS

WO    WO 93/18186       9/1993
WO    WO 2004/058945    7/2004

OTHER PUBLICATIONS

Barrett, et al., "Comparative genomic hybridization using oligonucleotide microarrays and total genomic DNA", Proc Natl Acad Sci, 2004, 101:17765-70.
Carter, et al., "Comparative analysis of comparative genomic hybridization microarray technologies: report of a workshop sponsored by the Wellcome Trust", Cytometry, 2002, 49:43-8.
Chen, et al., "Identification of clinically relevant viridans streptococci by an oligonucleotide array", J Clin Microbiol, 2005, 43:1515-21.
Cleary, et al., "Production of complex nucleic acid libraries using highly parallel in situ oligonucleotide synthesis", Nat Methods, 2004, 1:241-8.
Definition—Array—Merriam-Webster Dictionary, 1991, p. 104.
International Application No. PCT/US2007/066061, International Search Report dated Feb. 5, 2008.
Li, et al., "High resolution Analysis of DNA copy-number variations in the human genome with oligonucleotide microarrays", Applied Genomics and Proteomics, 2003, 2:93-100.
Mikhailovich, et al., "Identification of rifampin-resistant *Mycobacterium tuberculosis* strains by hybridization, PCR, and ligase detection reaction on oligonucleotide microchips", J Clin Microbiol, 2001, 39:2531-40.
Rouer, et al., "Structure of the human lck gene: differences in genomic organisation within src-related genes affect only N-terminal exons", Gene, 1989, 84:105-13.
Shuber, et al, "High throughput parallel analysis of hundreds of patient samples for more than 100 mutations in multiple disease genes", Hum Mol Genet, 1997, 6:337-47.
Speicher, et al., "The new cytogenetics: blurring the boundaries with molecular biology", Nat Rev Genet, 2005, 6:782-92.
Van Den Ijssel, et al., "Human and mouse oligonucleotide-based array CGH", Nucleic Acids Res, 2005, 33:e192.

*Primary Examiner* — Stephen Kapushoc
*Assistant Examiner* — Narayan Bhat

(57) ABSTRACT

The present invention generally relates to spatial and structural genomic analysis compositions, which can be used for the mapping of chromosomes and structural analyses of chromosomal rearrangements, including the entire chromosome, as well as specific portions or regions of interest of the chromosomes. In some embodiments, multiple portions of the genome can be distinguished, for instance, using a first detection entity and a second detection entity different from the first detection entity. The detection entities may be immobilized relative to oligonucleotides, which may be selected to bind to different locations within the chromosome. For instance, the oligonucleotides may be at least substantially complementary to the chromosome, e.g., substantially complementary to a specific location of the chromosome.

9 Claims, 3 Drawing Sheets

HIGH RESOLUTION CHROMOSOMAL MAPPING

CROSS REFERENCE TO RELATED APPLICATIONS

Pursuant to 35 U.S.C. §119(e), this application claims priority to recently allowed U.S. patent application Ser. No. 11/400,481, filed Apr. 7, 2006, the disclosure of which application is herein incorporated by reference.

BACKGROUND

Cytogenetics is typically used for identifying structures such as balanced translocations, marker chromosomes, and other genomic structures present in a sample of interest. Examples of cytogenetics techniques include Giemsa (G) banding, M banding, or spectral karyotyping (SKY). However these technologies are generally low resolution, and are often limited to the spatial resolution of the light microscope, e.g., several megabases. In addition techniques, such as M-banding require manual microdissection of the chromosomes of interest, e.g., under a light or fluorescence microscope. Therefore, structures of interest such as duplications, inversions, or translocations need to be at least several megabases (Mb) in length. Furthermore accurate and reproducible determination of the boundaries of genomic structures is limited by the relatively low resolution of these current techniques. Accordingly, there is a need to improve the spatial resolution of mapping and characterizing genomic structures.

SUMMARY OF THE INVENTION

The present invention generally relates to the mapping and structural analyses of chromosomes and chromosomal rearrangements. The subject matter of the present invention involves, in some cases, interrelated products, alternative solutions to a particular problem, and/or a plurality of different uses of one or more systems and/or articles.

In one aspect, the invention is an article. In one set of embodiments, the article comprises a physical genomic analysis composition. In some cases, the physical genomic analysis composition is constructed and arranged to be used in an assay of a nucleic acid. The composition may comprise a solution comprising a plurality of oligonucleotides, including at least a first oligonucleotide and a second oligonucleotide different from the first oligonucleotide. In some cases, each of the first and second oligonucleotides comprises respective first and second sequences each selected to hybridize to a selected region of interest in the nucleic acid used in the assay.

In one embodiment, the first oligonucleotide has a length of between 80 nucleotides and 200 nucleotides and the second oligonucleotide has a length of between 80 nucleotides and 200 nucleotides. In another embodiment, the first oligonucleotide has a length of between 100 nucleotides and 200 nucleotides and the second oligonucleotide has a length of between 100 nucleotides and 200 nucleotides. In some embodiments, the first oligonucleotide and/or the second oligonucleotide is present in solution in a predetermined amount and/or concentration. In one embodiment, the ratio of the concentration of the first oligonucleotide in solution to the concentration of the second oligonucleotide in solution is a predetermined ratio.

In some instances, the first oligonucleotide comprises a PCR primer sequence, and in some cases, the second oligonucleotide comprises an identical PCR primer sequence. The first oligonucleotide may also comprise a restriction endonuclease cleavage site and/or a portion thereof. In some embodiments, the solution comprises at least 100, at least 1,000, at least 10,000, or at least 100,000 non-identical oligonucleotides. The first sequence of the first oligonucleotide may be selected to hybridize to the nucleic acid has a length of at least 50 nucleotides, at least 100 nucleotides, or at least 150 nucleotides, in certain cases. The first oligonucleotide and the second oligonucleotide, in some embodiments, are synthesized from a substrate. The first sequence of the first oligonucleotide selected to hybridize to the nucleic acid may be perfectly complementary to a portion of the selected region of interest of the nucleic acid, and/or the second sequence of the second oligonucleotide selected to hybridize to the nucleic acid may be perfectly complementary to a second portion of the selected region of interest of the nucleic acid.

The nucleic acid is a genome, according to certain embodiments, for example, a mammalian genome, a human genome, a bacterial genome, or a viral genome. In some cases, the first oligonucleotide and the second oligonucleotide are designed using a computer. The region of interest may be a gene. In one embodiment, the first oligonucleotide has a predetermined sequence, and in some cases, the second oligonucleotide has a predetermined sequence.

The article comprises, in another set of embodiments, a solution comprising a plurality of oligonucleotides, at least some of which are not identical. In some embodiments, for at least a portion of the oligonucleotides, each of the oligonucleotides of the portion of oligonucleotides has a detection entity immobilized relative thereto. In certain cases, when the solution is exposed to a genome, at least some of the oligonucleotides of the portion of oligonucleotides interacts with the genome to cause portions of the genome to become distinguishable, where each distinguishable portion of the genome has a length of less than 1,000,000 bases, less than 100,000 bases, less than 10,000 bases, less than 1,000 bases, less than 500 bases, less than 300 bases, less than 100 bases, less than 50 bases, etc. In some cases, each of the oligonucleotides of the portion of oligonucleotides has a length of at least 80 nucleotides, at least 100 nucleotides, or at least 125 nucleotides, and in certain instances, the solution comprises at least 100 non-identical oligonucleotides, at least 1,000 non-identical oligonucleotides, at least 10,000 non-identical oligonucleotides, at least 100,000 non-identical oligonucleotides, etc. In one embodiment, each of the oligonucleotides of the portion of oligonucleotides comprises a restriction endonuclease cleavage site. Each of the oligonucleotides of the portion of oligonucleotides may also comprise a PCR primer recognition sequence. In certain cases, the detection entity is fluorescent, and/or comprises a dye.

The article, in one set of embodiments, includes an array comprising a physical genomic analysis composition, constructed and arranged to be used in an assay of a nucleic acid, the composition comprising a plurality of oligonucleotides, including at least a first oligonucleotide and a second oligonucleotide different from the first oligonucleotide, wherein each of the first and second oligonucleotides comprises respective first and second sequences each selected to hybridize to a selected region of interest in the nucleic acid used in the assay.

In yet another set of embodiments, the article comprises a solution comprising a plurality of oligonucleotides, at least some of which are not identical. In one embodiment, for at least a portion of the oligonucleotides, each of the oligonucleotides of the portion of oligonucleotides contains a region having a length of at least 10 nucleotides able to hybridize to a portion of a region of interest of the genome. In certain cases, for any portion of the region of interest having a length of at least about 1,000,000 bases, at least one of the oligonucleotides of the portion of oligonucleotides is able to hybridize to a section of the 1,000,000-base portion, the section having a length of at least 10 nucleotides.

In another aspect, the invention is a method. In one set of embodiments, the method comprises acts of providing a sample comprising a nucleic acid, and exposing the sample to a physical genomic analysis composition comprising a plurality of oligonucleotides, including at least a first oligonucleotide and a second oligonucleotide different from the first oligonucleotide. In some cases, each of the first and second oligonucleotides comprises respective first and second sequences each selected to hybridize to a selected region of interest in the nucleic acid used in the assay. The method also can include an act of determining hybridization of the plurality of oligonucleotides with the nucleic acid, and/or an act of analyzing the nucleic acid in the presence of the physical genomic analysis composition.

The method is a method of physically analyzing a genome, in another set of embodiments. The method may include acts of identifying a nucleic acid sequence, and designing at least a first oligonucleotide and a second oligonucleotide different from the first oligonucleotide. In some instances, each of the first and second oligonucleotides comprises respective first and second sequences each selected to hybridize the nucleic acid.

The act of designing may include using a computer, in some cases. The nucleic acid sequence can be part of a genome. In some embodiments, the act of identifying comprises identifying a first region and a second region of the genome, and designating the first region of the genome as the identified nucleic acid sequence, and in some cases, also identifying a region of interest of the genome, and designating the remainder of the genome as the identified nucleic acid sequence. In one embodiment, the method also includes acts of synthesizing the first oligonucleotide and the second oligonucleotide.

In yet another set of embodiments, the method is a method for mapping a genome. The method may include an act of exposing a genome to at least two detection entities such that each of the detection entities distinguishably associates with different portions of the genome. In some cases, each distinguishable portion of the genome has a length of less than 1,000,000 bases.

In one set of embodiments, the method is a method for mapping a genome. The method, in some cases, comprises acts of exposing a genome to a plurality of oligonucleotides, at least some of which are not identical, and distinguishing portions of the genome, each having lengths of less than 1,000,000 bases, using the detection entities. In some cases, for at least a portion of the oligonucleotides, each of the oligonucleotides of the portion of oligonucleotides has a detection entity immobilized relative thereto. Each distinguishable portion of the genome may also have a length of less than 100,000 bases, less than 10,000 bases, less than 1,000 bases, less than 500 bases, less than 300 bases, less than 100 bases, or less than 50 bases in some cases.

In still another set of embodiments, the method is a method for mapping a region of interest of a genome. The method may include acts of selecting a region of interest of a genome, and synthesizing a plurality of oligonucleotides, at least some of which are not identical. In some embodiments, for at least a portion of the oligonucleotides, each of the oligonucleotides of the portion of oligonucleotides contains a region having a length of at least 10 nucleotides able to hybridize to a portion of the region of interest of the genome. In certain instances, for any portion of the region of interest having a length of at least about 1,000,000 bases, at least one of the oligonucleotides of the portion of oligonucleotides is able to hybridize to a section of the 1,000,000-base portion. The section may have a length of at least 10 nucleotides In one set of embodiments, the method includes acts of identifying a selected region of interest of a nucleic acid, producing an array comprising a plurality of oligonucleotides, including at least a first oligonucleotide and a second oligonucleotide different from the first oligonucleotide, where each of the first and second oligonucleotides comprises respective first and second sequences each selected to hybridize to the selected region of interest of the nucleic acid, and cleaving one or more oligonucleotides off the array.

Yet another aspect of the invention is directed to a kit, for instance, a kit for use within an assay of a nucleic acid to physically analyze the nucleic acid. In one set of embodiments, the kit comprises a first oligonucleotide, and a second oligonucleotide different from the first oligonucleotide. In some cases, each of the first and second oligonucleotides comprises respective first and second sequences each selected to hybridize a sequence that is suspected of being present within the nucleic acid. The kit may also contain instructions for use of the first oligonucleotide and the second oligonucleotide.

In another aspect, the present invention is directed to a method of making one or more of the embodiments described herein. In another aspect, the present invention is directed to a method of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
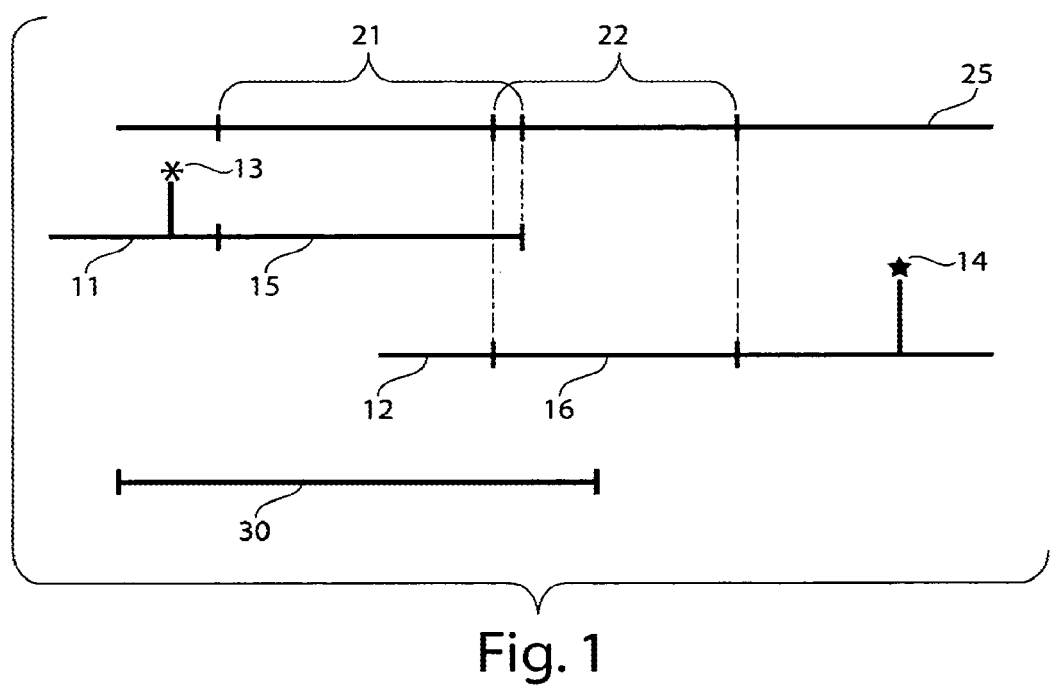
FIG. 1 schematically illustrates certain oligonucleotides of the invention, as used to map a portion of a genome, according to one embodiment of the invention.

DNA is a molecule that is present within all living cells. DNA encodes genetic instructions which tell the cell what to do. By "examining" the instructions, the cell can produce certain proteins or molecules, or perform various activities. DNA itself is a long, linear molecule where the genetic information is encoded using any one of four possible "bases," or molecular units, in each position along the DNA. This is roughly analogous to "beads on a string," where a string may have a large number of beads on it, encoding various types of information, although each bead along the string can only be of one of four different colors.

However, there are differences between each individual's DNA. In many cases, for an individual "gene" (essentially, a unit of information encoded within the DNA), the difference may be as subtle as a single base, or there may also be errors in the DNA. These errors may arise, for example, from various types of cancer.

In this invention, segments of nucleic acids are provided (called "oligonucleotides") which are "complementary" to the DNA and hence will stick to various portions to DNA. The oligonucleotides can also include a fluorescent entity, i.e., an entity that "glows" when exposed to certain types of light. Thus, the oligonucleotides can be applied to the DNA, then the DNA illuminated using certain types of light to see where the DNA "glows," which indicates where the oligonucleotides have bound to the DNA. In such a fashion, portions of DNA, or the entire DNA, can be "painted" using the techniques of the invention, making it easier to analyze the DNA.

More specifically, the present invention generally relates to the mapping of chromosomes and chromosomal rearrangements, including mapping of the entire chromosome, as well as specific portions or regions of interest of the chromosomes. In one aspect, relatively high resolution mapping of chromosomes can be achieved, e.g., resolutions of 1,000,000 bases, 1,000 bases, or even less in some cases. "Resolution" generally refers to regions or segments within the chromosome that can be distinguishably identified. In some embodiments, multiple portions of the genome can be distinguished, for instance, using a first detection entity and a second detection entity different from the first detection entity. The detection entities may be immobilized relative to oligonucleotides, which may be selected to bind to different locations within the chromosome. For instance, the oligonucleotides may be at least substantially complementary to the chromosome, e.g., substantially complementary to a specific location of the chromosome.

Certain aspects of the invention are directed to systems and methods for mapping genomes or portions of genomes, such as chromosomes. By exposing the genome to a plurality of oligonucleotides that can associate with specific regions of the genome, where at least some of the oligonucleotides are distinguishably labeled, e.g., with a detection entity, specific regions of the genome can be identified or studied. In some embodiments, as discussed below, regions of less than 1,000,000 bases within a genome can be distinguishably identified, and in some cases, regions of less than 100,000 bases, less than 10,000 bases, less than 1,000 bases, less than 500 bases, less than 300 bases, less than 100 bases, or even less than 50 bases within a genome can be distinguishably identified.

The genome can be from virtually any organism, for example, a human or non-human animal, for example, a mammal such as a dog, a cat, a horse, a donkey, a rabbit, a cow, a pig, a sheep, a goat, a rat, a mouse, a non-human primate (e.g., a monkey, a chimpanzee, a baboon, an ape, a gorilla, etc.); a bird such as a chicken, etc.; a reptile; an amphibian such as a toad or a frog; a fish such as a zebrafish; or the like. The genome can also come from other types of organisms, for example, plants, bacteria, viruses, fungi, molds, yeast, protists, viruses, or the like. The genome may be isolated from a cell, or from tissue, in some cases, as discussed below. The entire genome of an organism may be used in some embodiments. In other embodiments, however, the genome of the organism may be reduced in complexity prior to use. In still other embodiments, only portions of a genome of an organism may be used. For example, in one embodiment, a single chromosome of an organism may be used; in other embodiments, a subset of chromosomes from an organism may be used.

The term "genome," as used herein, refers to all nucleic acid sequences (coding and non-coding) and elements present in any virus, single cell (prokaryote or eukaryote) or each cell type in a metazoan organism. The term genome also applies to any naturally occurring or induced variation of these sequences that may be present in a mutant or disease variant of any virus, cell, or cell type. Genomic sequences include, but are not limited to, those involved in the maintenance, replication, segregation, and generation of higher order structures (e.g. folding and compaction of DNA in chromatin and chromosomes), or other functions, as well as all of the coding regions and their corresponding regulatory elements needed to produce and maintain each virus, cell, or cell type in a given organism.

For example, the human genome consists of approximately $3.0\times10^9$ base pairs (bp) of DNA, organized into distinct chromosomes. The genome of a normal diploid somatic human cell consists of 22 pairs of autosomes (chromosomes 1 to 22) and either chromosomes X and Y (males) or a pair of chromosome Xs (female), for a total of 46 chromosomes. A genome of a cancer cell may contain variable numbers of each chromosome in addition to deletions, rearrangements, and/or amplification of any subchromosomal region or DNA sequence. In certain embodiments, a genome refers to nuclear nucleic acids, excluding mitochondrial nucleic acids; however, in other embodiments, the term does not exclude mitochondrial nucleic acids. In still other aspects, the "mitochondrial genome" is used to refer specifically to nucleic acids found in mitochondrial fractions.

The genomic DNA used in various aspects of the invention may arise from any suitable genomic source. The "genomic source" is the source of the initial nucleic acids from which the nucleic acid probes are produced. The genomic source may be prepared using any convenient protocol. In some embodiments, the genomic source is prepared by first obtaining a starting composition of genomic DNA, e.g., a nuclear fraction of a cell lysate, where any convenient means for obtaining such a fraction may be employed and numerous protocols for doing so are well-known in the art. The genomic source is, in certain embodiments, genomic DNA representing the entire genome from a particular organism, tissue, or cell type. As an example, a given initial genomic source may be prepared from a subject, for example a plant or an animal, that is suspected of being homozygous or heterozygous for a deletion or amplification of a genomic region. In certain embodiments, the average size of the initial genomic source may have a size of at least about 1 Mb (1 Mb=1,000,000 bases), where a representative range of sizes is from about 50 Mb to about 250 Mb or more, while in other embodiments, the sizes may not exceed about 1 Mb, e.g., the genome may be about 1 Mb or smaller, e.g., less than about 500 kb (1 kb=1,000 bases), etc.

Mapping of the genome, or other nucleic acid, can be achieved, according to certain embodiments of the invention, by exposing the genome to a spatial or a physical genomic analysis composition, which may include an oligonucleotide able to distinguishably associate with different portions of the genome. Physical analysis of the genome includes both spatial and structural elements of a given genome. As used herein, a "spatial element" refers to the position or location of the sequence, for example, such that a certain sequence is duplicated (i.e., two copies) on chromosome 20q. A "structural element" also includes the orientation of the sequence, for instance, if the duplication is an inverted duplication.

The oligonucleotide may be immobilized relative to an detection entity. The oligonucleotides may contain a region having a length of at least 10 nucleotides that is substantially complementary to a portion of the genome. As used herein, a first, contiguous portion of a nucleic acid that is "substantially complementary" or is "able to hybridize" to a second, contiguous portion of a nucleic acid is one in which at least 75% of the first and second portions are complementary. In some embodiments, the two portions may be at least 80%, 85%, 90%, 95%, 96%, 97%, 98%, 99%, or 100% complementary (i.e., perfectly complementary). In other embodiments, the two portions may include a maximum of 0, 1, 2, 3, 4, 5, 6, 7, 8, 9, or 10 mismatches. The first and second portions may be at least substantially complementary for any suitable lengths of each of the two nucleic acids. For example, the two portions of the nucleic acids that are at least substantially complementary may each have complementary portions of at least 10 nucleotides, at least 30 nucleotides, at least 50 nucleotides, at least 100 nucleotides, at least 150 nucleotides, or at least 200 nucleotides. In some cases, the first and second portions are able to specifically bind to each other (i.e., the nucleic acids exhibit a high degree of specificity); for instance, the first and second portions may be able to bind to each other in a particular configuration or arrangement.

Each oligonucleotide may have any suitable length. For example, the length of the oligonucleotide may be between 60 nucleotides and 200 nucleotides (inclusive), between 80 nucleotides and 200 nucleotides, between 100 nucleotides and 200 nucleotides, between 125 nucleotides and 200 nucleotides, or between 150 nucleotides and 200 nucleotides. In some cases, the oligonucleotide may have a length of at least 60 nucleotides, at least 80 nucleotides, at least 100 nucleotides, or at least 150 nucleotides, and in certain embodiments, the oligonucleotide may have a length no greater than 200 nucleotides, no greater than 175 nucleotides, or no greater than 160 nucleotides. Oligonucleotides having such nucleotide lengths may be prepared using any suitable method, for example, using de novo DNA synthesis techniques known to those of ordinary skill in the art, such as solid-phase DNA synthesis techniques, or those techniques disclosed in U.S. patent application Ser. No. 11/234,701, filed Sep. 23, 2005, entitled "Methods for In Situ Generation of Nucleic Acid Molecules," incorporated herein by reference, or Cleary, et al., "Production of Complex Nucleic Acid Libraries using Highly Parallel in situ Oligonucleotide Synthesis," *Nature Methods,* 1(3):241-248 (2004), also incorporated herein by reference. Often, such oligonucleotides can be designed with the aid of a computer, based on the sequence of the genome and/or a region of interest, as discussed in more detail below.

In certain cases, more than one type of oligonucleotide (i.e., non-identical oligonucleotides) will be used, and each of the plurality of (types of) oligonucleotides can bind to various portions of the genome (i.e., more than one oligonucleotide may bind to the same portion of the genome, and/or to different portions of the genome, and/or to combinations thereof). For instance, there may be at least 100 non-identical types of oligonucleotides, at least 1,000 non-identical types of oligonucleotides, at least 10,000 non-identical types of oligonucleotides, or at least 100,000 non-identical types of oligonucleotides in solution. Of course, for each type of oligonucleotide, more than one identical molecule of the oligonucleotide may be present in solution. A nucleotide may be present in a known or predetermined amount or concentration, or in a known or predetermined ratio, relative to other oligonucleotides in solution. Techniques for preparing such oligonucleotides are discussed below.

Thus, various embodiments of the invention include a composition comprising 2 or more non-identical oligonucleotides, e.g., as described above, such as 3 or more oligonucleotides, 4 or more oligonucleotides, 5 or more oligonucleotides, 6 or more oligonucleotides, 7 or more oligonucleotides, 10 or more oligonucleotides, 20 or more oligonucleotides, 30 or more oligonucleotides, 40 or more oligonucleotides, 50 or more oligonucleotides, 60 or more oligonucleotides, 70 or more oligonucleotides, 80 or more oligonucleotides, 90 or more oligonucleotides, 100 or more oligonucleotides, 300 or more oligonucleotides, 500 or more oligonucleotides, 1,000 or more oligonucleotides, 3,000 or more oligonucleotides, 5,000 or more oligonucleotides, 10,000 or more oligonucleotides, etc. The relative amounts and/or concentrations of the different oligonucleotides in the composition may be the same or different. In certain embodiments, the concentration of each different oligonucleotide is known. For example, in some cases, the concentration of each is less than about 10 micromolar, less than about 5 micromolar, or less than about 3 micromolar. The concentration may also be less than about 1 micromolar, for instance, between about 0.1 micromolar to about 0.8 micromolar, such as from about 0.2 micromolar to about 0.5 micromolar. The oligonucleotides may be present in an aqueous fluid, e.g., water, saline, PBS, etc., where the fluid may or may not include further components, e.g., salts, solvents, surfactants, buffers, emulsifiers, chelating agents, etc.

The invention contemplates, in some aspects, "coverage" of the entire genome, or of a portion of the genome, with the plurality of oligonucleotides. Coverage of every single nucleotide within the genome is not necessary, and the oligonucleotides may be designed (e.g., as discussed below) such that only certain portions of the genome are covered, and/or such that certain genomic "windows" above a certain size are covered by the oligonucleotides. For instance, the "window" may have a length of at least 1,000,000 bases, i.e., such that for any portion of the genome having a length of at least about 1,000,000 bases, at least one oligonucleotide molecule is substantially complementary to a section of that 1,000,000-base portion. Such a portion of the genome is said to be "covered." Smaller windows, i.e., higher resolutions, are also contemplated in certain embodiments. For example, the "window" may have a size of at least 10,000 bases, at least 10,000 bases, at least 5,000 bases, at least 3,000 bases, at least 1,000 bases, at least 750 bases, at least 500 bases, at least 300 bases, at least 200 bases, at least 150 bases, at least 100 bases, or at least 50 bases.

By way of example, referring now to FIG. 1, a first oligonucleotide 11 may include a region 15 substantially complementary to a first portion 21 of nucleic acid 25, while a second oligonucleotide 12 may include a region 16 substantially complementary to a second portion 22 of nucleic acid 25. First portion 21 and second portion 22 may or may not be overlapping within nucleic acid 15. If window 30 has a length of 100 bases, no part of nucleic acid 25 can be covered by window 30 without also covering at least one of portions 21 or 22. Thus, for a window the size of window 30, no matter where the window is positioned within nucleic acid 25, at least one of oligonucleotides 11 and 12 is able to bind to at least a portion of the window. In some cases, higher-resolution (i.e., smaller) windows may be used. For instance, the window may have a length of less than 1,000 nucleotides, less than 500 nucleotides, less than 300 nucleotides, less than 100 nucleotides, less than 50 nucleotides, less than 30 nucleotides, or less than 10 nucleotides. It should be noted that, as depicted in FIG. 1, the entire oligonucleotide (oligonucleotides 11 and 12) does not necessarily have to be substantially complementary to nucleic acid 25. As discussed below, the oligonucleotide may also include other regions that do not interact with nucleic acid 25.

For genomic regions that are longer than the oligonucleotides, the genomic region can be "tiled" by (non-identical) oligonucleotides to provide suitable coverage. For instance, as is illustrated in FIG. 1, a first oligonucleotide 11 may include a region 15 substantially complementary to a first portion 21 of nucleic acid 25, while a second oligonucleotide 12 may include a region 16 substantially complementary to a second portion 22 of nucleic acid 25. First portion 21 and second portion 22 may or may not be overlapping within nucleic acid 25. However, due to the presence of oligonucleotides 11 and 12, both portions 21 and 22 of nucleic acid 25 are suitably covered. This "tiling" process can be extended as necessary to cover larger genomic regions, or even the entire genome.

In some cases, substantially all of the genome may be covered using oligonucleotides, e.g., by using tiling. However, in other embodiments, only certain portions of the genome may be covered using oligonucleotides, e.g., a chromosome, or a portion thereof may be covered. Essentially any length of the genome may be covered, e.g., by using "tiling" to achieve coverage. For instance, portions of the genome (which may be contiguous in some cases) of at least about 100,000 bases, at least about 1,000,000 bases, at least about 3,000,000 bases, or at least about 10,000,000 bases may be covered.

In one embodiment, substantially all of the genome is covered. However, in other embodiments, only a region of interest is covered. Thus, the oligonucleotides may be selected to associate primarily with the region of interest, which is typically contiguous (i.e., without any breaks). Of course, there may be some non-specific binding outside of the region of interest by the oligonucleotides, but in general, the oligonucleotides will exhibit substantial complementarity with a sequence contained within the region of interest for portions that are at least 10 nucleotides long, or in some cases, at least 30 nucleotides, at least 50 nucleotides, at least 100 nucleotides, at least 150 nucleotides, or at least 200 nucleotides long. In other embodiments, there may be more than one such region of interest, for example, 2, 3, 4, 5, 6, etc. regions of interest.

The region of interest within the genome may be of any suitable size. In one embodiment, the region of interest has a length of at least 100 nucleotides. In other embodiments, the region of interest may have a length of at least 150 nucleotides, at least 200 nucleotides, at least 300 nucleotides, at least 500 nucleotides, at least 1,000 nucleotides, at least 3,000 nucleotides, at least 5,000 nucleotides, at least 10,000 nucleotides, at least 30,000 nucleotides, at least 50,000 nucleotides, at least 100,000 nucleotides, at least 300,000 nucleotides, at least 500,000 nucleotides, or at least 1,000,000 nucleotides. In one embodiment, the region of interest is a single chromosome; in other embodiments, a subset of chromosomes may be used.

The region of interest may be located in any portion of the genome, and perform any function (or no function) within the genome. For instance, the region of interest may be a locus, a gene, a promoter, an enhancer, a terminator, an exon or intron, a splice region, junk DNA, origins of replication, telomeres, or the like. The region of interest may exhibit (or is suspected to exhibit) certain abnormalities, such as additions, deletions, duplications, rearrangements, breakpoints, inversions, homologous or non-homologous recombination, garbling, or the like, and thus, genomes with these abnormalities can be readily determined. Additional non-limiting examples include aneuploidy, unbalanced translocations, amplifications, insertions, heterogeneity, single copy losses, homozygous deletions, as well as amplicons of variable sizes within the genome. In one embodiment, the region of interest is a region of the genome having a non-natural or non-normal copy number. As used herein, a "copy number" is given its ordinary meaning as used in the art, i.e., the number of times a certain nucleic acid sequence appears within a genome. The copy number of a genome may be altered by amplifying or deleting sequences within a normal genome, thereby producing a non-natural copy number. Variations in copy number detectable by the systems and methods of the invention may arise in different ways. For example, the copy number may be altered as a result of the amplification or deletion of a chromosomal region, e.g. as commonly occurs in cancer, thereby producing a non-natural copy number.

The region of interest can be selected using any suitable technique, or may be chosen based on relevant knowledge. In one embodiment, the region of interest is determined using a cytogenetic assay, such as those disclosed in Speicher, et al., "The New Cytogenetics: Blurring the Boundaries with Molecular Biology," *Nature Reviews Genetics*, 6:782-792 (2004), incorporated herein by reference. For example, the region of interest may be selected using a comparative genomic hybridization (CGH) technique, for instance, array-based comparative genomic hybridization (aCGH). Non-limiting examples of techniques for CGH have been disclosed in U.S. patent application Ser. No. 10/744,595, filed Dec. 22, 2003, entitled "Comparative Genomic Hybridization Assays using Immobilized Oligonucleotide Features and Compositions for Practicing the Same," by Bruhn, et al., published as U.S. Patent Application Publication No. 2004/0191813 on Sep. 30, 2004; U.S. patent application Ser. No. 10/448,298, filed May 28, 2003, entitled "Comparative Genomic Hybridiztion Assays using Immobilized Oligonucleotide Targets with Initially Small Sample Sizes and Compositions for Practicing the Same," by Barrett, et al., published as U.S. Patent Application Publication No. 2004/0241658 on Dec. 2, 2004; and International Patent Application No. PCT/US 2003/041047, filed Dec. 22, 2003, entitled "Comparative Genomic Hybridization Assays using Immobilized Oligonucleotide Features and Compositions for Practicing the Same," by Bruhn, et al., published as WO 2004/058945 on Jul. 15, 2004; each incorporated herein by reference. Additional details of CGH and aCGH are discussed below.

As mentioned, the entire oligonucleotide does not have to be substantially complementary with portions of the genome. Thus, the oligonucleotide may contain other sequences as well. For instance, the oligonucleotide may contain PCR primer sequences, cleavage sites, repetitive sequences, junk or random sequences, control sequences (e.g., a promoter, an enhancer, and/or a terminator sequence), sequences used to control the $T_m$ (melting temperature) of the oligonucleotide, etc.

In one embodiment, the oligonucleotide includes a primer sequence, such as a PCR primer sequence. As is known to those of ordinary skill in the art, a primer sequence is typically a relatively short, often artificial sequence that can be used to "amplify" or make duplications of a nucleic acid sequence, using well-established techniques such as PCR (polymerase chain reaction). The primer sequence may have a length of between 15 nucleotides and 50 nucleotides, and typically between 18 nucleotides and 25 nucleotides. An oligonucleotide having a primer sequence may be amplified (i.e., may identical copies made of the oligonucleotide), e.g., for use in subsequent assays. Those of ordinary skill in the art will be well-aware of suitable primer sequences that can be incorporated into the oligonucleotide.

In yet another embodiment, the oligonucleotide may be designed to have a particular melting temperature ($T_m$) or range of melting temperatures. The $T_m$ of a given oligonucleotide can be predicted or calculated by those of ordinary skill in the art, for example, based on the primary sequence of the oligonucleotide and the numbers of nucleotides that are present. Thus, by designing the oligonucleotide to have certain nucleotides and/or certain distributions of nucleotides, oligonucleotides having certain predetermined $T_m$s can be readily designed.

In still another embodiment, the oligonucleotide includes a "cleavage site," i.e. a site within the nucleic acid that can be specifically cleaved, e.g., with a restriction endonuclease, light, or with certain chemicals. Those of ordinary skill in the art will be familiar with restriction endonucleases, and restriction sites that are recognized by the restriction endonucleases. Typically, the restriction site for a restriction endonuclease is palindromic. The restriction site may be located within the oligonucleotide in any suitable position. For instance, the restriction site may be located towards one end of the oligonucleotide. In certain cases, the oligonucleotide may include more than one cleavage site. The cleavage site typically has a length of 4 nucleotides, 6 nucleotides, or 8 nucleotides, although other lengths are also possible.

As mentioned, more than one oligonucleotide may be designed having one or more these features, e.g., a first oligonucleotide and a second oligonucleotide may bind a common region of the genome (or portion thereof), or different regions within the genome, and have different primary sequences. Thus, a plurality of non-identical oligonucleotides may be designed. In some cases, relatively large numbers of non-identical oligonucleotides may be designed. For instance, at least 5, at least 10, at least 30, at least 50, at least 100, at least 500, at least 1,000, at least 5,000, at least 10,000, at least 50,000, or at least 100,000 non-identical oligonucleotides may be designed, and in some cases, each having certain features in common, for example, one or more restriction sites in common.

In some embodiments, a detection entity is immobilized relative to the oligonucleotide. The detection entity may be immobilized to the oligonucleotide either prior to, or after, exposure of the oligonucleotide to the genome. As used herein, a "detection entity" is an entity that is capable of indicating its existence in a particular sample or at a particular location. One non-limiting example of a detection entity is a fluorescent moiety. Detection entities of the invention can be those that are identifiable by the unaided human eye, those that may be invisible in isolation but may be detectable by the unaided human eye if in sufficient quantity, entities that absorb or emit electromagnetic radiation at a level or within a wavelength range such that they can be readily detected visibly (unaided or with a microscope including a fluorescence microscope or an electron microscope, or the like), spectroscopically, or the like. Non-limiting examples include fluorescent moieties (including phosphorescent moieties), radioactive moieties, electron-dense moieties, dyes, chemiluminescent entities, electrochemiluminescent entities, enzyme-linked signaling moieties, etc. In some cases, the detection entity itself is not directly determined, but instead interacts with a second entity (a "signaling entity") in order to effect determination (e.g., a primary antibody that recognizes the detection entity, and a labeled secondary antibody that recognizes the primary antibody). Thus, for example, coupling of the signaling entity to the detection entity may result in a determinable signal. The detection entity may be covalently attached to the oligonucleotide as a separate entity (e.g., a fluorescent molecule), or the detection entity may be integrated within the nucleic acid, for example, covalently or as an intercalation entity, as a detectable sequence of nucleotides within the oligonucleotide, etc. In some cases, the detection entity (or at least a portion thereof) forms part of the primary structure of the oligonucleotide. For instance, a number of different nucleic acid labeling protocols are known in the art and may be employed to produce a population of labeled oligonucleotides. The particular protocol may include the use of labeled primers, labeled nucleotides, nucleic acid analogs, modified nucleotides that can be conjugated with different dyes, one or more amplification steps, etc.

A variety of different detection entities may be employed, for example, fluorescent entities, isotopic entities, enzymatic entities, particulate entities, etc, as described above. Any combination of entities, e.g. first and second entities, first, second and third entities, etc., may be employed for various embodiments. Examples of distinguishable detection entities are well known in the art and include: two or more different emission wavelength fluorescent dyes, like Cy3 and Cy5, or Alexa 542 and Bodipy 630/650; two or more isotopes with different energy of emission, like $^{32}P$ and $^{33}P$; labels which generate signals under different treatment conditions, like temperature, pH, treatment by additional chemical agents, etc.; and detection entities which generate signals at different time points after treatment. Using one or more enzymes for signal generation allows for the use of an even greater variety of distinguishable detection entities based on different substrate specificity of enzymes (e.g. alkaline phosphatase/peroxidase).

If more than one oligonucleotide is used, each of the oligonucleotides may be immobilized relative to the same, or different, types of detection entities. For instance, a first oligonucleotide, able to bind to a first region of the genome, may have immobilized relative thereto a first detection entity, while a second oligonucleotide, able to bind to a first region of the genome, may have immobilized relative thereto a second detection entity, which may be the same or different from the first detection entity. For multiple oligonucleotides, by optimizing the sequences of each oligonucleotide and the detection entities immobilized relative thereto, very high resolution mappings can be obtained. For instance, regions of less than 1,000,000 bases within a genome can be distinguishably identified, and in some cases, regions of less than 100,000 bases, less than 10,000 bases, less than 1,000 bases, less than 500 bases, less than 300 bases, less than 100 bases, or even less than 50 bases within a genome can be distinguishably identified.

As an example, referring now to FIG. 1, oligonucleotide 11 may have a first detection entity 13 immobilized relative thereto, while oligonucleotide 12 may have a second detection entity 14 immobilized relative thereto. In some cases, first detection entity 13 and second detection entity 14 are indistinguishable; thus, region 20 of genomic portion 25 can be determined by determining association of the detection entities with genomic portion 25. In other cases, however, first detection entity 13 and second detection entity 14 can be distinguished, for example, first detection entity 13 and second detection entity 14 may have different fluorescence emission wavelengths. Here, first portion 21 of genomic portion 25 can be distinguished from second portion 22 by determining the respective locations of first detection entity 13 and second detection entity 14.

The oligonucleotides may be prepared using any suitable method, e.g., de novo DNA synthesis techniques known to those of ordinary skill in the art, such as solid-phase DNA synthesis techniques, or these techniques described in U.S. patent application Ser. No. 11/234,701, filed Sep. 23, 2005, entitled "Methods for In Situ Generation of Nucleic Acid Molecules," incorporated herein by reference. For instance, multiple oligonucleotide molecules (which each independently may be the same, or different, depending on the application) may be grown on a substrate (e.g., starting from the 3' end of the oligonucleotide, such that the 5' end of the oligonucleotide is furthest away from the surface of the substrate), then some or all of the oligonucleotides may be released from the substrate, for example chemically, or by using enzymes such as restriction endonucleases (if the oligonucleotides comprise cleavage sites, e.g., near their 3' ends). In some cases, a first group of oligonucleotides may be released from the substrate using a first enzyme able to recognize a first cleavage site common to the first group of oligonucleotides, while a second group of oligonucleotides may be released from the substrate using a second enzyme able to recognize a second cleavage site common to the second group of oligonucleotides, but not the first group of oligonucleotides. Thus, separate groups of oligonucleotides can be released independently of each other.

In some embodiments, the oligonucleotides can be designed, e.g., by a computer, prior to synthesis, in some cases based on the sequence of genome and/or the region of interest. For example, a plurality of oligonucleotides may be prepared that includes sequences substantially complementary to portions of the genome, or to portions present within the region of interest. The oligonucleotide may also comprise one or more primer sequences, cleavage sites, etc., depending on the application, and any of these sequences may be present within the oligonucleotide in any suitable order.

In some cases, precursor oligonucleotides (such as those described above) are synthesized on a substrate (e.g., as described herein), then the precursor oligonucleotides are removed or cleaved from the substrate to produce the final oligonucleotide(s). For example, the precursor oligonucleotides may comprise one or more cleavage sites, which can be cleaved under suitable conditions, e.g., by exposure to a restriction endonuclease, light, or with certain chemicals (e.g., a base). In one set of embodiments, the precursor oligonucleotides are prepared on an array, then the final oligonucleotides are produced by cleaving the precursor oligonucleotides from the array.

In some cases, other oligonucleotides other than those described above may also be present in solution. For example, the solution may contain a nonzero fraction of the oligonucleotide molecules described above, and optionally, another fraction of oligonucleotides having characteristics and properties other than those described above. The nonzero fraction of the oligonucleotide molecules of the invention present in solution may be any suitable fraction, for example, at least about 10%, at least about 20%, at least about 30%, at least about 40%, at least about 50%, at least about 60%, at least about 70%, at least about 80%, or at least about 90%.

Another aspect of the invention is generally directed to a kit. A "kit," as used herein, typically defines a package including one or more of the compositions of the invention, and/or other compositions associated with the invention, for example, one or more oligonucleotides as previously described. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, flits, filters, rings, clamps, wraps, patches, containers, and the like, for example, for using, modifying, assembling, storing, packaging, preparing, mixing, diluting, and/or preserving the compositions components for a particular use.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, assembly, storage, packaging, and/or preparation of the compositions and/or other compositions associated with the kit. In some cases, the instructions may also include instructions, for example, for a particular use. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

The kits may also comprise containers, each with one or more of the various reagents and/or compositions. The kits may also include a collection of immobilized oligonucleotide targets, e.g., one or more arrays of targets, and reagents employed in genomic template and/or labeled probe production, e.g., a highly processive polymerase, exonuclease resistant primers, random primers, buffers, the appropriate nucleotide triphosphates (e.g. dATP, dCTP, dGTP, dTTP), DNA polymerase, labeling reagents, e.g., labeled nucleotides, or the like. The kits may further include labeling reagents for making two or more collections of distinguishably labeled nucleic acids according to the subject methods, an array of target nucleic acids, hybridization solution, etc.

The following documents are incorporated herein by reference: U.S. patent application Ser. No. 10/448,298, filed May 28, 2003, entitled "Comparative Genomic Hybridization Assays using Immobilized Oligonucleotide Targets with Initially Small Sample Sizes and Compositions for Practicing the Same," by Barrett, et al., published as U.S. Patent Application Publication No. 2004/0241658 on Dec. 2, 2004; and International Patent Application No. PCT/US2003/041047, filed Dec. 22, 2003, entitled "Comparative Genomic Hybridization Assays using Immobilized Oligonucleotide Features and Compositions for Practicing the Same," by Bruhn, et al., published as WO 2004/058945 A2 on Jul. 15, 2004. Also incorporated herein by reference is a patent application entitled "Competitive Oligonucleotides," by Barrett, et al., and a patent application entitled "Validation of Comparative Genomic Hybridization," by Barrett, et al., each filed on even date herewith.

Unless defined otherwise, all technical and scientific terms used herein have the same meaning as commonly understood by one of ordinary skill in the art to which this invention belongs. Still, certain terms are defined below for the sake of clarity and ease of reference.

As used herein, the term "determining" generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction.

The term "sample," as used herein, relates to a material or mixture of materials, typically, although not necessarily, in fluid form, containing one or more components of interest. Samples include, but are not limited to, samples obtained from an organism or from the environment (e.g., cells, tissue, a soil sample, water sample, etc.) and may be directly obtained from a source (e.g., such as a biopsy or from a tumor) or indirectly obtained, e.g., after culturing and/or one or more processing steps. In some embodiments, samples are a complex mixture of molecules, e.g., comprising at least about 50 different molecules, at least about 100 different molecules, at least about 200 different molecules, at least about 500 different molecules, at least about 1000 different molecules, at least about 5000 different molecules, at least about 10,000 molecules, etc.

When two items are "associated" with one another, they are provided in such a way that it is apparent one is related to the other such as where one references the other. For example, an array identifier can be associated with an array by being on the array assembly (such as on the substrate or a housing) that carries the array or on or in a package or kit carrying the array assembly.

"Stably attached" or "stably associated with" means an item's position remains substantially constant.

"Contacting" means to bring or put together. As such, a first item is contacted with a second item when the two items are brought or put together, e.g., by touching them to each other.

"Depositing" means to position, place an item at a location, or otherwise cause an item to be so positioned or placed at a location. Depositing includes contacting one item with another. Depositing may be manual or automatic, e.g., "depositing" an item at a location may be accomplished by automated robotic devices.

The term "biomolecule" means any organic or biochemical molecule, group or species of interest. The biomolecule may be formed in an array on a substrate surface. Non-limiting examples of biomolecules include peptides, proteins, amino acids, and nucleic acids.

A "biopolymer" is a polymer of one or more types of repeating units. Biopolymers are typically found in biological systems and include polysaccharides (such as carbohydrates), peptides (which term is used to include polypeptides and proteins, whether or not attached to a polysaccharide), and polynucleotides, as well as their analogs, such as those compounds composed of or containing amino acid analogs or non-amino acid groups, or nucleotide analogs or non-nucleotide groups. As such, this term includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes deoxyribonucleic acid or DNA (including cDNA), ribonucleic acid or RNA and oligonucleotides, regardless of the source. A "biomonomer" refers to a single unit, which can be linked with the same or other biomonomers to form a biopolymer (e.g., a single amino acid or nucleotide with two linking groups, one or both of which may have removable protecting groups). A biomonomer fluid or biopolymer fluid refers to a liquid containing either a biomonomer or biopolymer, respectively, typically in solution.

The term "peptide," as used herein, refers to any compound produced by amide formation between a carboxyl group of one amino acid and an amino group of another group. The term "oligopeptide," as used herein, refers to peptides with fewer than about 10 to 20 residues, i.e., amino acid monomeric units. As used herein, the term "polypeptide" refers to peptides with more than 10 to 20 residues. The term "protein," as used herein, refers to polypeptides of specific sequence of more than about 50 residues.

As used herein, the term "amino acid" is intended to include not only the L, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, epsilon-nicotinoyl-lysine, isonipecotic acid, tetrahydroisoquinoleic acid, alpha acid, sarcosine, citrulline, cysteic acid, t-butylglycine, t-butylalanine, phenylglycine, cyclohexylalanine, beta-alanine, 4-aminobutyric acid, and the like.

The term "ligand" as used herein refers to a moiety that is capable of covalently or otherwise chemically binding a compound of interest. The arrays of solid-supported ligands produced by the methods can be used in screening or separation processes, or the like, to bind a component of interest in a sample. The term "ligand" in the context of the invention may or may not be an "oligomer" as defined above. However, the term "ligand" as used herein may also refer to a compound that is "pre-synthesized" or obtained commercially, and then attached to the substrate.

The term "monomer" as used herein refers to a chemical entity that can be covalently linked to one or more other such entities to form a polymer. Of particular interest to the present application are nucleotide "monomers" that have first and second sites (e.g., 5' and 3' sites) suitable for binding to other like monomers by means of standard chemical reactions (e.g., nucleophilic substitution), and a diverse element which distinguishes a particular monomer from a different monomer of the same type (e.g., a nucleotide base, etc.). In the art, synthesis of nucleic acids of this type may utilize, in some cases, an initial substrate-bound monomer that is generally used as a building-block in a multi-step synthesis procedure to form a complete nucleic acid.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include, but are non limited to, deoxyribonucleotides (DNA), ribonucleotides (RNA), or other polynucleotides which are C-glycosides of a purine or pyrimidine base. The oligomer may be defined by, for example, about 2-500 monomers, about 10-500 monomers, or about 50-250 monomers.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "nucleic acid" as used herein means a polymer composed of nucleotides, e.g., deoxyribonucleotides or ribonucleotides, or compounds produced synthetically (e.g. PNA as described in U.S. Pat. No. 5,948,902) which can hybridize with naturally occurring nucleic acids in a sequence specific manner analogous to that of two naturally occurring nucleic acids, e.g., can participate in Watson-Crick base pairing interactions. The terms "ribonucleic acid" and "RNA," as used herein, refer to a polymer comprising ribonucleotides. The terms "deoxyribonucleic acid" and "DNA," as used herein, mean a polymer comprising deoxyribonucleotides. The term "oligonucleotide" as used herein denotes single stranded nucleotide multimers of from about 10 to 200 nucleotides and up to about 500 nucleotides in length. For instance, the oligonucleotide may have a length greater than about 60 nucleotides, greater than about 80 nucleotides, greater than about 100 nucleotides, greater than about 125 nucleotides, or greater than about 150 nucleotides.

As used herein, a "target nucleic acid sample" or a "target nucleic acid" refer to nucleic acids comprising sequences whose quantity or degree of representation (e.g., copy number) or sequence identity is being assayed. Similarly, "test genomic acids" or a "test genomic sample" refers to genomic nucleic acids comprising sequences whose quantity or degree of representation (e.g., copy number) or sequence identity is being assayed.

As used herein, a "reference nucleic acid sample" or a "reference nucleic acid" refers to nucleic acids comprising sequences whose quantity or degree of representation (e.g., copy number) or sequence identity is known. Similarly, "reference genomic acids" or a "reference genomic sample" refers to genomic nucleic acids comprising sequences whose quantity or degree of representation (e.g., copy number) or sequence identity is known. A "reference nucleic acid sample" may be derived independently from a "test nucleic acid sample," i.e., the samples can be obtained from different organisms or different cell populations of the sample organism. However, in certain embodiments, a reference nucleic acid is present in a "test nucleic acid sample" which comprises one or more sequences whose quantity or identity or degree of representation in the sample is unknown while containing one or more sequences (the reference sequences) whose quantity or identity or degree of representation in the sample is known. The reference nucleic acid may be naturally present in a sample (e.g., present in the cell from which the sample was obtained) or may be added to or spiked in the sample.

A "nucleotide" refers to a sub-unit of a nucleic acid and has a phosphate group, a 5-carbon sugar and a nitrogen-containing base, as well as functional analogs (whether synthetic or naturally occurring) of such sub-units which, in the polymer form (as a polynucleotide), can hybridize with naturally occurring polynucleotides in a sequence specific manner analogous to that of two naturally occurring polynucleotides. Nucleotide sub-units of deoxyribonucleic acids are deoxyribonucleotides, and nucleotide sub-units of ribonucleic acids are ribonucleotides.

The terms "nucleoside" and "nucleotide" are intended to include those moieties that contain not only the known purine and pyrimidine base moieties, but also other heterocyclic base moieties that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Generally, as used herein, the terms "oligonucleotide" and "polynucleotide" are used interchangeably. Further, generally, the term "nucleic acid" or "nucleic acid molecule" also encompasses oligonucleotides and polynucleotides.

If a nucleic acid or probe "corresponds to" a chromosome, the polynucleotide usually contains a sequence of nucleic acids that is unique to that chromosome. Accordingly, a polynucleotide that corresponds to a particular chromosome usually specifically hybridizes to a labeled nucleic acid made from that chromosome, relative to labeled nucleic acids made from other chromosomes. Array elements, because they usually contain polynucleotides, can also correspond to a chromosome.

A "non-cellular chromosome composition" is a composition of chromosomes synthesized by mixing pre-determined amounts of individual chromosomes. These synthetic compositions can include selected concentrations and ratios of chromosomes that do not naturally occur in a cell, including any cell grown in tissue culture. Non-cellular chromosome compositions may contain more than an entire complement of chromosomes from a cell, and, as such, may include extra copies of one or more chromosomes from that cell. Non-cellular chromosome compositions may also contain less than the entire complement of chromosomes from a cell.

The terms "hybridize" or "hybridization," as is known to those of ordinary skill in the art, refer to the binding or duplexing of a nucleic acid molecule to a particular nucleotide sequence under suitable conditions, e.g., under stringent conditions. The term "stringent conditions" (or "stringent hybridization conditions") as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent conditions are the summation or combination (totality) of both hybridization and wash conditions.

Stringent conditions (e.g., as in array, Southern or Northern blotting or hybridizations) may be sequence dependent, and are often different under different experimental parameters. Stringent conditions that can be used to hybridize nucleic acids include, for instance, hybridization in a buffer comprising 50% formamide, 5×SSC (salt, sodium citrate), and 1% SDS at 42° C., or hybridization in a buffer comprising 5×SSC and 1% SDS at 65° C., both with a wash of 0.2×SSC and 0.1% SDS at 65° C. Other examples of stringent conditions include a hybridization in a buffer of 40% formamide, 1 M NaCl, and 1% SDS at 37° C., and a wash in 1×SSC at 45° C. In another example, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional examples of stringent conditions include hybridization at 60° C. or higher and 3×SSC (450 mM sodium chloride/45 mM sodium citrate) or incubation at 42° C. in a solution containing 30% formamide, 1 M NaCl, 0.5% sodium lauryl sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to another nucleic acid (for example, when a nucleic acid has hybridized to a nucleic acid probe). Wash conditions used to identify nucleic acids may include, e.g., a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1×SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate. The terms "high stringency conditions" or "highly stringent hybridization conditions," as previously described, generally refers to conditions that are compatible to produce complexes between complementary binding members, i.e., between immobilized probes and complementary sample nucleic acids, but which does not result in any substantial complex formation between non-complementary nucleic acids (e.g., any complex formation which cannot be detected by normalizing against background signals to interfeature areas and/or control regions on the array).

Stringent hybridization conditions may also include a "pre-hybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA, or the like.

Additional hybridization methods are described in references describing CGH techniques (Kallioniemi, et al., *Science*, 258:818-821, 1992 and WO 93/18186). Several guides to general techniques are available, e.g., Tijssen, *Hybridization with Nucleic Acid Probes*, Parts I and II (Elsevier, Amsterdam 1993). For a descriptions of techniques suitable for in situ hybridizations see, e.g., Gall et al. *Meth. Enzymol.* 1981; 21:470-480 and Angerer, et al., *In Genetic Engineering: Principles and Methods*, Setlow and Hollaender, Eds. Vol 7, pgs 43-65 (Plenum Press, New York 1985). See also U.S. Pat. Nos. 6,335,167, 6,197,501, 5,830,645, and 5,665,549, the disclosures of which are herein incorporated by reference.

The phrases "nucleic acid molecule bound to a surface of a solid support," "probe bound to a solid support," "probe immobilized with respect to a surface," "target bound to a solid support," or "polynucleotide bound to a solid support" (and similar terms) generally refer to a nucleic acid molecule (e.g., an oligonucleotide or polynucleotide) or a mimetic thereof (e.g., comprising at least one PNA, UNA, and/or LNA monomer) that is immobilized on the surface of a solid substrate, where the substrate can have a variety of configurations, e.g., including, but not limited to, planar substrates, non-planar substrate, a sheet, bead, particle, slide, wafer, web, fiber, tube, capillary, microfluidic channel or reservoir, or other structure. The solid support may be porous or non-porous. In certain embodiments, collections of nucleic acid molecules are present on a surface of the same support, e.g., in the form of an array, which can include at least about two nucleic acid molecules. The two or more nucleic acid molecules may be identical or comprise a different nucleotide base composition.

Certain embodiments of the invention include arrays, for example, a nucleic acid array. An "array," includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. The term "feature" is used interchangeably herein, in this context, with the terms: "features," "feature elements," "spots," "addressable regions," "regions of different moieties," "surface or substrate immobilized elements" and "array elements," where each feature is made up of oligonucleotides bound to a surface of a solid support, also referred to as substrate immobilized nucleic acids. By "immobilized" is meant that the moiety or moieties are stably associated with the substrate surface in the region, such that they do not separate from the region under conditions of using the array, e.g., hybridization and washing conditions. As is known in the art, the moiety or moieties may be covalently or non-covalently bound to the surface in the region. For example, each region may extend into a third dimension in the case where the substrate is porous while not having any substantial third dimension measurement (thickness) in the case where the substrate is non-porous. Arrays of nucleic acids are known in the art, where representative arrays that may be modified to become arrays of the subject invention as described herein, include those described in: U.S. Pat. Nos. 6,656,740; 6,613,893; 6,599,693; 6,589,739; 6,587,579; 6,420,180; 6,387,636; 6,309,875; 6,232,072; 6,221,653; and 6,180,351 and the references cited therein.

In the broadest sense, the arrays of many embodiments are arrays of polymeric binding agents, where the polymeric binding agents may be any one or more of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). In some cases, the arrays are arrays of polypeptides, e.g., proteins or fragments thereof.

The arrays may be provided by any convenient means, including obtaining them from a commercial source or by synthesizing them de novo. To synthesize an array, in one embodiment, the first step is generally to determine the nature of the mixture of nucleic acids that is to be produced. For example, in those embodiments where the nucleic acid mixture is to be employed as a reference or control in a differential gene expression application, as described in greater detail herein, the first step is to identify those genes that are to be assayed in the particular protocol to be performed. Following identification of these genes, the specific region, i.e., stretch or domain, of each product nucleic acid to which the probe nucleic acid is to hybridize can then be identified. Any convenient method may be employed to determine the sequences of the surface immobilized nucleic acids, including probe design algorithms, including but not limited to those algorithms described in U.S. Pat. No. 6,251,588 and published U.S. Application Nos. 2004/0101846; 2004/0101845; 2004/0086880; 2004/0009484; 2004/0002070; 2003/0162183 and 2003/0054346; the disclosures of which are herein incorporated by reference. Following identification of the probe sequences as defined above, an array may be produced in which some or all of the probe sequences of the identified set are present.

The array may also bear nucleic acids, particularly oligonucleotides or synthetic mimetics thereof (i.e., the oligonucleotides defined above), and the like. Where the arrays are arrays of nucleic acids, the nucleic acids may be adsorbed, physisorbed, chemisorbed, or covalently attached to the arrays at any point or points along the nucleic acid chain.

The methods described herein may result in the production of a plurality of nucleic acids, where each of the different variable domains of the template array is represented in the plurality, i.e., for each feature present on the template array, there is at least one nucleic acid in the plurality that corresponds to the feature. The length of the nucleic acids may be, for instance, from about 20 nucleotide to about 500 nucleotide or longer, such as from about 50 nucleotide to about 200 nucleotide, including from about 60 nucleotide to about 100 nucleotide. The plurality of nucleic acids produced in some embodiments may be characterized by having a known composition. By known composition is meant that, because of the way in which the plurality is produced, the sequence of each distinct nucleic acid in the product plurality can be predicted with a high degree of confidence. Accordingly, assuming no infidelities, the sequence of each individual or distinct nucleic acid in the product plurality is known. In many embodiments, the relative amount or copy number of each distinct nucleic acid of differing sequence in the plurality is known.

For those embodiments where the product plurality is a mixture, the term mixture refers to a heterogenous composition of a plurality of different nucleic acids that differ from each other by sequence. Accordingly, the mixtures produced by the subject methods may be viewed as compositions of two or more nucleic acids that are not chemically combined with each other and are capable of being separated, e.g., by using an array of complementary surface immobilized nucleic acids, but are not in fact separated.

A "CGH" array or an "aCGH" array refers to an array that can be used to compare DNA samples for relative differences in copy number. These will now be described in greater detail. In general, an aCGH array can be used in any assay in which it is desirable to scan a genome with a sample of nucleic acids. For example, an aCGH array can be used in location analysis as described in U.S. Pat. No. 6,410,243, the entirety of which is incorporated herein and thus can also be referred to as a "location analysis array" or an "array for ChIP-chip analysis." In certain aspects, a CGH array provides probes for screening or scanning a genome of an organism and comprises probes from a plurality of regions of the genome.

In using an array in the present invention, the array will be exposed in certain embodiments to a sample (for example, a fluorescently labeled target nucleic acid molecule) and the array then read. Reading of the array may be accomplished, for instance, by illuminating the array and reading the location and intensity of resulting fluorescence at various locations of the array (e.g., at each spot or element) to detect any binding complexes on the surface of the array. For example, a scanner may be used for this purpose which is similar to the AGILENT MICROARRAY SCANNER scanner available from Agilent Technologies, Palo Alto, Calif. Other suitable apparatus and methods are described in U.S. Pat. No. 6,756,202 or 6,406,849, each incorporated herein by reference.

A "CGH assay" using an aCGH array can be generally performed as follows. In one embodiment, a population of nucleic acids contacted with an aCGH array comprises at least two sets of nucleic acid populations, which can be derived from different sample sources. For example, in one aspect, a target population contacted with the array comprises a set of target molecules from a reference sample and from a test sample. In one aspect, the reference sample is from an organism having a known genotype and/or phenotype, while the test sample has an unknown genotype and/or phenotype or a genotype and/or phenotype that is known and is different from that of the reference sample. For example, in one aspect, the reference sample is from a healthy patient while the test sample is from a patient suspected of having cancer or known to have cancer.

In one embodiment, a target population being contacted to an array in a given assay comprises at least two sets of target populations that are differentially labeled (e.g., by spectrally distinguishable labels). By "differentially labeled" is meant that the nucleic acids are labeled differently from each other such that they can be simultaneously distinguished from each other. In one aspect, control target molecules in a target population are also provided as two sets, e.g., a first set labeled with a first label and a second set labeled with a second label corresponding to first and second labels being used to label reference and test target molecules, respectively.

In one set of embodiments, the control target molecules in a population are present at a level comparable to a haploid amount of a gene represented in the target population. In other embodiments, the control target molecules are present at a level comparable to a diploid amount of a gene. In still other embodiments, the control target molecules are present at a level that is different from a haploid or diploid amount of a gene represented in the target population. The relative proportions of complexes formed labeled with the first label vs. the second label can be used to evaluate relative copy numbers of targets found in the two samples.

In certain embodiments, test and reference populations of nucleic acids may be applied separately to separate but identical arrays (e.g., having identical probe molecules) and the signals from each array can be compared to determine relative copy numbers of the nucleic acids in the test and reference populations.

Arrays may also be read by any other method or apparatus than the foregoing, with other reading methods, including other optical techniques (for example, detecting chemiluminescent or electroluminescent labels) or electrical techniques (where each feature is provided with an electrode to detect hybridization at that feature in a manner disclosed in, e.g., U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample or an organism from which a sample was obtained exhibits a particular condition).

The term "substrate" as used herein refers to a surface upon which marker molecules or probes, e.g., an array, may be adhered. Glass slides are the most common substrate for biochips, although fused silica, silicon, plastic, and other materials are also suitable.

The substrate may be formed in essentially any shape. In one set of embodiments, the substrate has at least one surface which is substantially planar. However, in other embodiments, the substrate may also include indentations, protuberances, steps, ridges, terraces, or the like. The substrate may be formed from any suitable material, depending upon the application. For example, the substrate may be a silicon-based chip or a glass slide. Other suitable substrate materials for the arrays of the present invention include, but are not limited to, glasses, ceramics, plastics, metals, alloys, carbon, agarose, silica, quartz, cellulose, polyacrylamide, polyamide, polyimide, and gelatin, as well as other polymer supports or other solid-material supports. Polymers that may be used in the substrate include, but are not limited to, polystyrene, poly(tetra)fluoroethylene (PTFE), polyvinylidenedifluoride, polycarbonate, polymethylmethacrylate, polyvinylethylene, polyethyleneimine, polyoxymethylene (POM), polyvinylphenol, polylactides, polymethacrylimide (PMI), polyalkenesulfone (PAS), polypropylene, polyethylene, polyhydroxyethylmethacrylate (HEMA), polydimethylsiloxane, polyacrylamide, polyimide, various block co-polymers, etc.

Any given substrate may carry any number of oligonucleotides on a surface thereof. In some cases, one, two, three, four, or more arrays may be disposed on a surface of the substrate. Depending upon the use, any or all of the arrays may be the same or different from one another and each may contain multiple spots, or elements or features. A typical array may contain more than ten, more than one hundred, more than one thousand, more ten thousand features, or even more than one hundred thousand features, in an area of less than 20 cm$^2$ or even less than 10 cm$^2$. For example, features may have widths (that is, diameter, for a round spot) in the range from a 10 micrometers to 1.0 cm. In other embodiments each feature may have a width in the range of 1.0 micrometers to 1.0 mm, 5.0 micrometers to 500 micrometers, 10 micrometers to 200 micrometers, etc. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas may be present in some embodiments which do not carry any oligonucleotide (or other biopolymer or chemical moiety of a type of which the features are composed). Such interfeature areas may be present where the arrays are formed by processes involving drop deposition of reagents but may not be present when, for example, light directed synthesis fabrication processes are used. It will be appreciated though, that the interfeature areas, when present, could be of various sizes and configurations.

The substrate may have thereon a pattern of locations (or elements) (e.g., rows and columns) or may be unpatterned or comprise a random pattern. The elements may each independently be the same or different. For example, in certain cases, at least about 25% of the elements are substantially identical (e.g., comprise the same sequence composition and length). In certain other cases, at least 50% of the elements are substantially identical, or at least about 75% of the elements are substantially identical. In certain cases, some or all of the elements are completely or at least substantially identical. For instance, if nucleic acids are immobilized on the surface of a solid substrate, at least about 25%, at least about 50%, or at least about 75% of the oligonucleotides may have the same length, and in some cases, may be substantially identical.

An "array layout" or "array characteristics" refers to one or more physical, chemical or biological characteristics of the array, such as positioning of some or all the features within the array and on a substrate, one or more dimensions of the spots or elements, or some indication of an identity or function (for example, chemical or biological) of a moiety at a given location, or how the array should be handled (for example, conditions under which the array is exposed to a sample, or array reading specifications or controls following sample exposure).

Each array may cover an area of less than 100 cm2, or even less than 50 cm2, 10 cm2, 1 cm$^2$, 0.5 cm$^2$, or 0.1 cm$^2$. In certain embodiments, the substrate carrying the one or more arrays will be shaped as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. In some cases, the array will have a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm. In some instances, with arrays that are read by detecting fluorescence, the substrate may be of a material that emits low fluorescence upon illumination with the excitation light. Additionally, in some cases the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident thereon, as may be measured across the entire integrated spectrum of such illuminating light or alternatively at 532 nm or 633 nm.

In certain embodiments of particular interest, in situ prepared arrays are employed. In situ prepared oligonucleotide arrays, e.g., nucleic acid arrays, may be characterized by having surface properties of the substrate that differ significantly between the feature and interfeature areas. Specifically, such arrays may have high surface energy, hydrophilic features and hydrophobic, low surface energy hydrophobic interfeature regions. Whether a given region, e.g., feature or interfeature region, of a substrate has a high or low surface energy can be readily determined by determining the regions "contact angle" with water, as known in the art and further described in copending application Ser. No. 10/449,838, the disclosure of which is herein incorporated by reference. Other features of in situ prepared arrays that make such array formats of particular interest in certain embodiments of the present invention include, but are not limited to: feature density, oligonucleotide density within each feature, feature uniformity, low intra-feature background, low interfeature background, e.g., due to hydrophobic interfeature regions, fidelity of oligonucleotide elements making up the individual features, array/feature reproducibility, and the like. The above benefits of in situ produced arrays assist in maintaining adequate sensitivity while operating under stringency conditions required to accommodate highly complex samples.

In certain embodiments, a nucleic acid sequence may be present as a composition of multiple copies of the nucleic acid molecule on the surface of the array, e.g., as a spot or element on the surface of the substrate. The spots may be present as a pattern, where the pattern may be in the form of organized rows and columns of spots, e.g., a grid of spots, across the substrate surface, a series of curvilinear rows across the substrate surface, e.g., a series of concentric circles or semi-circles of spots, or the like. The density of spots present on the array surface may vary, for example, at least about 10, at least about 100 spots/cm$^2$, at least about 1,000 spots/cm$^2$, or at least about 10,000 spots/cm$^2$. In other embodiments, however, the elements are not arranged in the form of distinct spots, but may be positioned on the surface such that there is substantially no space separating one element from another.

In certain aspects, in constructing arrays, both coding and non-coding genomic regions are included as probes, whereby "coding region" refers to a region comprising one or more exons that is transcribed into an mRNA product and from there translated into a protein product, while by non-coding region it is meant any sequences outside of the exon regions, where such regions may include regulatory sequences, e.g., promoters, enhancers, untranslated but transcribed regions, introns, origins of replication, telomeres, etc. In certain embodiments, one can have at least some of the oligonucleotides directed to non-coding regions and others directed to coding regions. In certain embodiments, one can have all of the oligonucleotides directed to non-coding sequences and such sequences can, optionally, be all non-transcribed sequences (e.g., intergenic regions including regulatory sequences such as promoters and/or enhancers lying outside of transcribed regions).

In certain aspects, an array may be optimized for one type of genome scanning application compared to another, for example, the array can be enriched for intergenic regions compared to coding regions for a location analysis application. In some embodiments, at least 5% of the polynucleotide probes on the solid support hybridize to regulatory regions of a sample of interest, while other embodiments may have at least 30% of the polynucleotide probes on the solid support hybridize to exonic regions of a sample of interest. In yet other embodiments, at least 50% of the polynucleotide probes on the solid support hybridize to intergenic regions (e.g., non-coding regions which exclude introns and untranslated regions, i.e, comprise non-transcribed sequences) of a nucleotide sample of interest.

In certain aspects, oligonucleotide probes on the array represent random selection of genomic sequences (e.g., both coding and noncoding). However, in other aspects, particular regions of the genome are selected for representation on the array, e.g., such as CpG islands, genes belonging to particular pathways of interest or whose expression and/or copy number are associated with particular physiological responses of interest (e.g., disease, such a cancer, drug resistance, toxo- logical responses and the like). In certain aspects, where particular genes are identified as being of interest, intergenic regions proximal to those genes are included on the array along with, optionally, all or portions of the coding sequence corresponding to the genes. In one aspect, at least about 100 bp, 500 bp, 1,000 bp, 5,000 bp, 10,000 kb or even 100,000 kb of genomic DNA upstream of a transcriptional start site is represented on the array in discrete or overlapping sequence probes. In certain aspects, at least one probe sequence comprises a motif sequence to which a protein of interest (e.g., such as a transcription factor) is known or suspected to bind.

In certain aspects, repetitive sequences are excluded as probes on the arrays. However, in another aspect, repetitive sequences are included.

The choice of nucleic acids to use as probes may be influenced by prior knowledge of the association of a particular chromosome or chromosomal region with certain disease conditions. Int. Pat. Apl. WO 93/18186 provides a list of exemplary chromosomal abnormalities and associated diseases, which are described in the scientific literature. Alternatively, whole genome screening to identify new regions subject to frequent changes in copy number can be performed using the methods of the present invention discussed further below.

In some embodiments, previously identified regions from a particular chromosomal region of interest are used as probes. In certain embodiments, the array can include probes which tile a particular region (e.g., which have been identified in a previous assay or from a genetic analysis of linkage), as previously discussed. The probes may correspond to a region of interest as well as genomic sequences found at defined intervals on either side, i.e., 5' and 3' of, the region of interest, where the intervals may or may not be uniform, and may be tailored with respect to the particular region of interest and the assay objective. In other words, the tiling density may be tailored based on the particular region of interest and the assay objective. Such "tiled" arrays and assays employing the same are useful in a number of applications, including applications where one identifies a region of interest at a first resolution, and then uses a tiled array tailored to the initially identified region to further assay the region at a higher resolution, e.g., in an iterative protocol.

In certain aspects, the array includes probes to sequences associated with diseases associated with chromosomal imbalances for prenatal testing. For example, in one aspect, the array comprises probes complementary to all or a portion of chromosome 21 (e.g., Down's syndrome), all or a portion of the X chromosome (e.g., to detect an X chromosome deficiency as in Turner's Syndrome) and/or all or a portion of the Y chromosome, Klinefelter Syndrome (to detect duplication of an X chromosome and the presence of a Y chromosome), all or a portion of chromosome 7 (e.g., to detect William's Syndrome), all or a portion of chromosome 8 (e.g., to detect Langer-Giedon Syndrome), all or a portion of chromosome 15 (e.g., to detect Prader-Willi or Angelman's Syndrome, all or a portion of chromosome 22 (e.g., to detect Di George's syndrome).

Other "themed" arrays may be fabricated, for example, arrays including whose duplications or deletions are associated with specific types of cancer (e.g., breast cancer, prostate cancer and the like). The selection of such arrays may be based on patient information such as familial inheritance of particular genetic abnormalities. In certain aspects, an array for scanning an entire genome is first contacted with a sample and then a higher-resolution array is selected based on the results of such scanning. Themed arrays also can be fabricated for use in gene expression assays, for example, to detect expression of genes involved in selected pathways of interest, or genes associated with particular diseases of interest.

In one embodiment, a plurality of probes on the array are selected to have a duplex $T_m$, within a predetermined range. For example, in one aspect, at least about 50% of the probes have a duplex $T_m$ within a temperature range of about 75° C. to about 85° C. In one embodiment, at least 80% of said polynucleotide probes have a duplex $T_m$ within a temperature range of about 75° C. to about 85° C., within a range of about 77° C. to about 83° C., within a range of from about 78° C. to about 82° C. or within a range from about 79° C. to about 82° C. In one aspect, at least about 50% of probes on an array have range of $T_m$'s of less than about 4° C., less then about 3° C., or even less than about 2° C., e.g., less than about 1.5° C., less than about 1.0° C. or about 0.5° C.

The probes on the microarray, in certain embodiments, have a nucleotide length in the range of at least 30 nucleotides to 200 nucleotides, or in the range of at least about 30 to about 150 nucleotides. In other embodiments, at least about 50% of the polynucleotide probes on the solid support have the same nucleotide length, and that length may be about 60 nucleotides.

In still other aspects, probes on the array comprise at least coding sequences. In one aspect, probes represent sequences from an organism such as *Drosophila melanogaster, Caenorhabditis elegans*, yeast, zebrafish, a mouse, a rat, a domestic animal, a companion animal, a primate, a human, etc. In certain aspects, probes representing sequences from different organisms are provided on a single substrate, e.g., on a plurality of different arrays.

Figure 2:
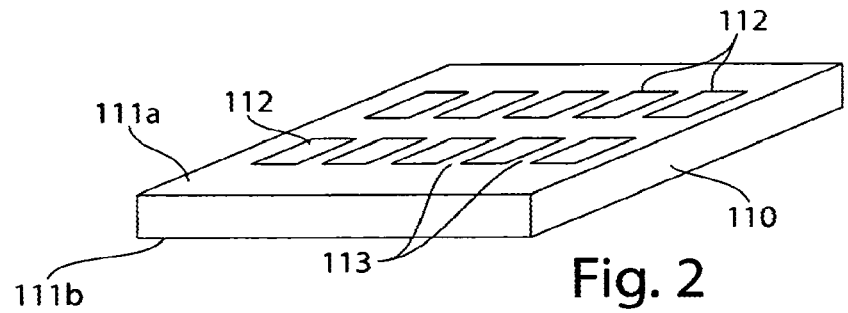
FIG. 2 shows an example of a substrate carrying an array, in accordance with one embodiment of the invention.
Figure 3:
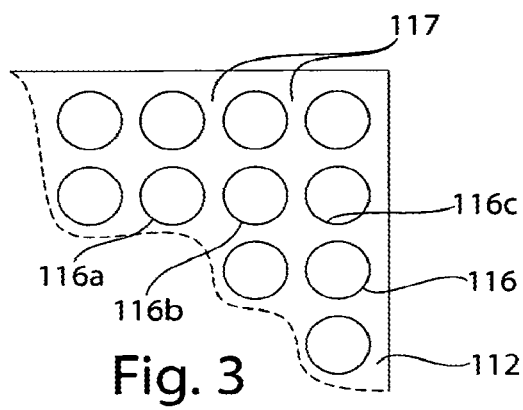
FIG. 3 shows an enlarged view of a portion of FIG. 2.
Figure 4:
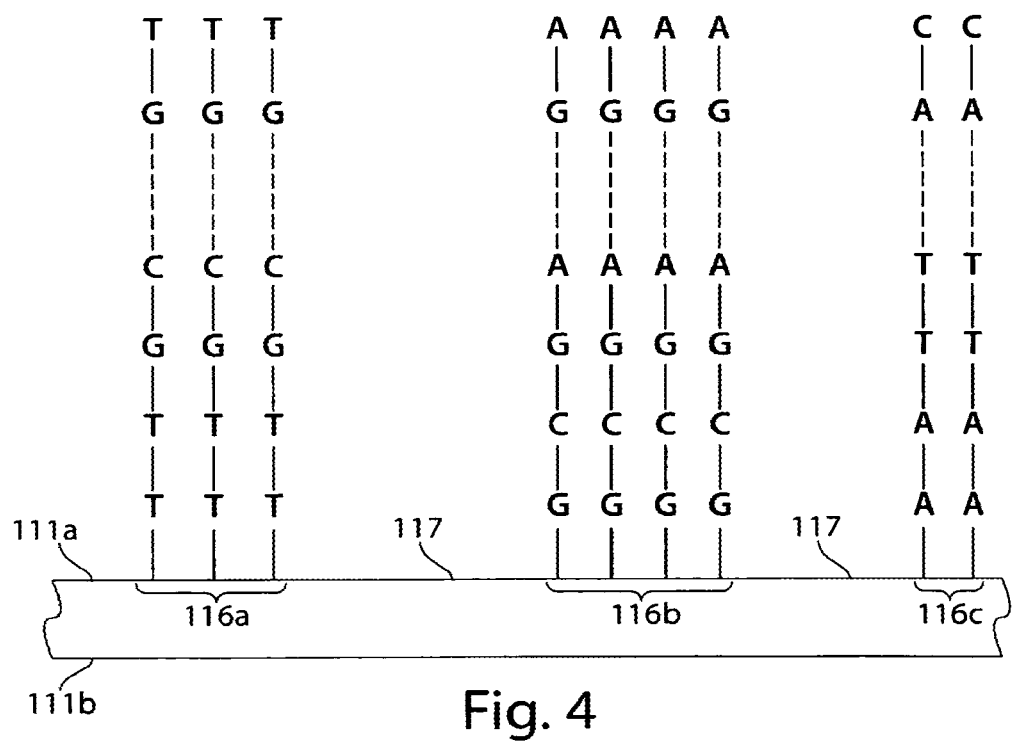
FIG. 4 shows an enlarged view of another portion of the substrate of FIG. 2.

In some embodiments, the array may be referred to as addressable. An array is "addressable" when it has multiple regions of different moieties (e.g., different nucleic acids) such that a region (i.e., an element or "spot" of the array) at a particular predetermined location (i.e., an "address") on the array may be used to detect a particular target or class of targets (although an element may incidentally detect non-targets of that element). In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., nucleic acid molecules, to be evaluated by binding with the other). An example of an array is shown in FIGS. 2-4, where the array shown in this representative embodiment includes a contiguous planar substrate 110 carrying an array 112 disposed on a rear surface 111*b* of substrate 110. It will be appreciated though, that more than one array (any of which are the same or different) may be present on rear surface 111*b*, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the rear surface 111*b*, with regions of the rear surface 111*b* adjacent the opposed sides 113*c*, 113*d* and leading end 113*a* and trailing end 113*b* of slide 110, not being covered by any array 112. A front surface 111*a* of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of oligomers, e.g., in the form of polynucleotides, and specifically oligonucleotides. As mentioned above, all of the features 116 may be different, or some or all could be the same. The interfeature areas 117 could be of various sizes and configurations. Each feature carries a predetermined oligomer such as a predetermined polynucleotide (which includes the possibility of mixtures of polynucleotides). It will be understood that there may be a linker molecule (not shown) of any known types between the rear surface 111*b* and the first nucleotide.

Substrate 110 may carry on front surface 111*a*, an identification code, e.g., in the form of bar code (not shown) or the like printed on a substrate in the form of a paper label attached by adhesive or any convenient means. The identification code contains information relating to array 112, where such information may include, but is not limited to, an identification of array 112, i.e., layout information relating to the array(s), etc.

In the case of an array in the context of the present application, the "target" may be referenced as a moiety in a mobile phase (typically fluid), to be detected by "probes" which are bound to the substrate at the various regions.

A "scan region" refers to a contiguous (preferably, rectangular) area in which the array spots or elements of interest, as discussed above, are found. For example, the scan region may be that portion of the total area illuminated from which resulting fluorescence is detected and recorded. For the purposes of this invention, the scan region includes the entire area of the slide scanned in each pass of the lens, between the first element of interest, and the last element of interest, even if there exist intervening areas which lack elements of interest. An "array layout" refers to one or more characteristics of the features, such as element positioning on the substrate, one or more feature dimensions, and an indication of a moiety at a given location.

In one aspect, the array comprises probe sequences for scanning an entire chromosome arm, wherein probes targets are separated by at least about 500 bp, at least about 1 kb, at least about 5 kb, at least about 10 kb, at least about 25 kb, at least about 50 kb, at least about 100 kb, at least about 250 kb, at least about 500 kb and at least about 1 Mb. In another aspect, the array comprises probes sequences for scanning an entire chromosome, a set of chromosomes, or the complete complement of chromosomes forming the organism's genome. By "resolution" is meant the spacing on the genome between sequences found in the probes on the array. In some embodiments (e.g., using a large number of probes of high complexity) all sequences in the genome can be present in the array. The spacing between different locations of the genome that are represented in the probes may also vary, and may be uniform, such that the spacing is substantially the same between sampled regions, or non-uniform, as desired. An assay performed at low resolution on one array, e.g., comprising probe targets separated by larger distances, may be repeated at higher resolution on another array, e.g., comprising probe targets separated by smaller distances.

The arrays can be fabricated using drop deposition from pulsejets of either oligonucleotide precursor units (such as monomers) in the case of in situ fabrication, or the previously obtained oligonucleotide. Such methods are described in detail in, for example, in U.S. Pat. No. 6,242,266, 6,232,072, 6,180,351, 6,171,797, or 6,323,043, or in U.S. patent application Ser. No. 09/302,898, filed Apr. 30, 1999, and the references cited therein. These are each incorporated herein by reference. Other drop deposition methods can be used for fabrication, as previously described herein.

The following examples are intended to illustrate certain embodiments of the present invention, but do not exemplify the full scope of the invention.

Example 1

This example illustrates one method of mapping the boundaries of a genomic structure, according to one embodiment of the invention.

Figure 5:
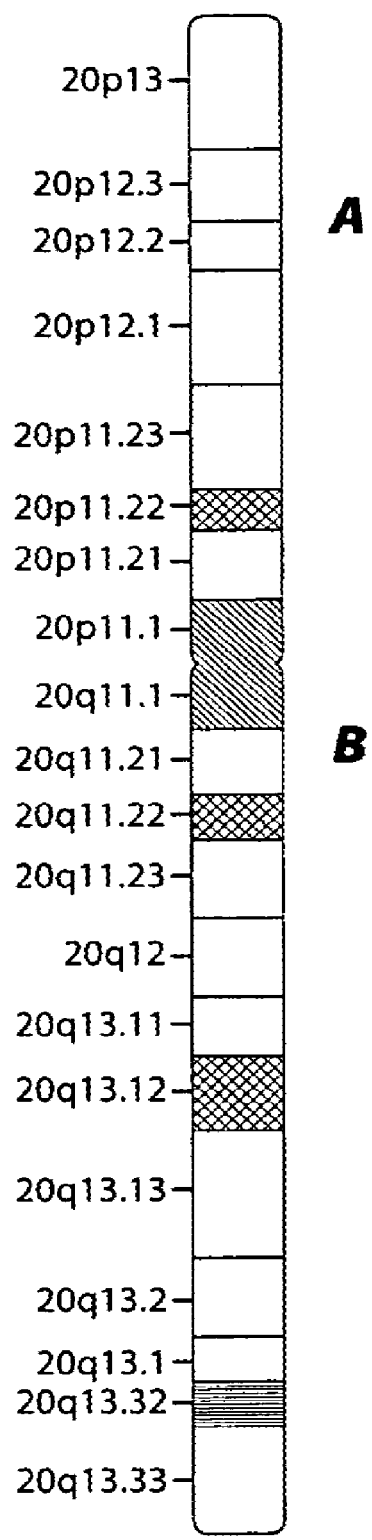
FIG. 5 shows cytogenetic G-bands in Chromosome 20, in one embodiment of the invention.

Chromosome 20 has 20 cytogenetic G-bands (20p13-20q13.33), as shown schematically in FIG. 5. A series of design probes of pools of long oligonucleotides were prepared. For the "p" arm, each pool included unique genomic sequences within a cytoband. The 5' and 3' ends of cytoband-specific pool precisely defined by DNA sequence.

For the "q" arm, each pool included unique genomic sequences of <100 kb within a single G band (e.g. 20q12). The 5' and 3' ends of each sub-cytoband pool were precisely defined by DNA sequence.

The sequences within individual cytobands can be precisely synthesized as individual pools of long oligonucleotides. These can also be used to provide high resolution mapping of any genomic structures within these regions.

It will be appreciated that throughout the present application, that words such as "cover," "base," "front," "back," and "top" are used in a relative sense only. The word "above" used to describe the substrate and/or flow cell is meant with respect to the horizontal plane of the environment, e.g., the room, in which the substrate and/or flow cell is present, e.g., the ground or floor of such a room.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described. All definitions, as defined and used herein, should be understood to control over dictionary definitions, definitions in documents incorporated by reference, and/or ordinary meanings of the defined terms.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. In this specification and the appended claims, the singular forms "a," "an" and "the" include plural reference unless the context clearly dictates otherwise.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

"Optional" or "optionally," as used herein, means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

It should also be understood that, unless clearly indicated to the contrary, in any methods claimed herein that include more than one step or act, the order of the steps or acts of the method is not necessarily limited to the order in which the steps or acts of the method are recited.

All publications mentioned herein are incorporated herein by reference for the purpose of describing and disclosing the invention components that are described in the publications that might be used in connection with the presently described invention.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising:
   a) contacting a target nucleic acid with a solution to produce a hybridized sample, said solution comprising a mixture of at least 5 different labeled oligonucleotides that specifically bind to a region in a mammalian chromosome, wherein said labeled oligonucleotides:
      i. are complementary to a unique sequence in said region;
      ii. are of 80 to 200 nucleotides in length; and
      iii. include a labeled oligonucleotide comprising a nucleotide sequence that overlaps with a nucleotide sequence in another labeled oligonucleotide in said mixture, wherein said labeled oligonucleotides, when hybridized to said mammalian chromosome, are tiled across said region; and
   b) imaging said hybridized sample to a provide a binding pattern for said labeled oligonucleotides.

2. The method of claim 1, wherein said target nucleic acid is an intact mammalian chromosome.

3. The method of claim 1, wherein imaging is done by reading fluorescence.

4. The method of claim 1, wherein said chromosome is a human chromosome.

5. The method of claim 1, wherein said solution further comprises labeled oligonucleotides that bind to said region and do not overlap with another labeled oligonucleotide in said mixture.

6. The method of claim 1, wherein said solution comprises oligonucleotides that are distinguishably labeled from the oligonucleotides in said mixture.

7. The method of claim 1, wherein said oligonucleotides comprise a PCR primer sequence.

8. The method of claim 1, wherein said oligonucleotides comprise a restriction endonuclease cleavage site.

9. The method of claim 1, wherein said oligonucleotides are synthesized on a solid support in an array, cleaved from said array, and then labeled.

* * * * *

UNITED STATES PATENT AND TRADEMARK OFFICE
CERTIFICATE OF CORRECTION

| | | |
|---|---|---|
| PATENT NO. | : 8,309,307 B2 | Page 1 of 1 |
| APPLICATION NO. | : 13/286975 | |
| DATED | : November 13, 2012 | |
| INVENTOR(S) | : Michael Thomas Barrett et al. | |

It is certified that error appears in the above-identified patent and that said Letters Patent is hereby corrected as shown below:

In column 32, line 12, in Claim 1, before "provide" delete "a".

Signed and Sealed this
Second Day of April, 2013

Teresa Stanek Rea
*Acting Director of the United States Patent and Trademark Office*